United States Patent
Simmen

[11] Patent Number: 5,766,258
[45] Date of Patent: Jun. 16, 1998

[54] WRIST PROSTHESIS

[75] Inventor: Beat R. Simmen, Tagelswangen, Switzerland

[73] Assignee: Plus Endoprothetik Ag, Switzerland

[21] Appl. No.: 700,390

[22] PCT Filed: Feb. 23, 1995

[86] PCT No.: PCT/EP95/00664

§ 371 Date: Nov. 11, 1996

§ 102(e) Date: Nov. 11, 1996

[87] PCT Pub. No.: WO95/22945

PCT Pub. Date: Aug. 31, 1995

[30] Foreign Application Priority Data

Feb. 24, 1994 [DE] Germany ............... 44 06 090.4

[51] Int. Cl.[6] ........................................ A61F 2/42
[52] U.S. Cl. ............................................. 623/21
[58] Field of Search .......................... 623/18, 21

[56] References Cited

U.S. PATENT DOCUMENTS

| 4,229,841 | 10/1980 | Youm et al. ............... 623/21 |
| 4,307,473 | 12/1981 | Weber ........................ 623/21 |
| 4,714,476 | 12/1987 | Ranawat et al. ......... 623/21 |

FOREIGN PATENT DOCUMENTS

| 0342014 | 11/1989 | European Pat. Off. ........ 623/23 |
| 0532440 | 3/1991 | European Pat. Off. ........ 623/21 |
| 9316763 | 1/1994 | Germany ........................ 623/21 |
| 8302555 | 8/1983 | WIPO ........................ 623/18 |

Primary Examiner—David Isabella
Attorney, Agent, or Firm—Andrus, Sceales, Starke & Sawall

[57] ABSTRACT

A wrist prosthesis has a radial part and a metacarpal part (12). A joint connection (15) connects the radial and the metacarpal parts including shafts for placement in the metacarpal bone and the carpal regions. The joint connection (15) is biaxial and permits both dorsal/palmar flexion and radial/ulnar deflection. The radial/ulnar flexion has a swivel radius ($R_1$). The dorsal/palmar flexion has a swivel radius ($R_2$). The radius ($R_1$) is greater than the radius ($R_2$). The contacting joint surfaces are congruent in all relative positions. A separate collar is provided for slipping onto the shaft of the radial part. The collar has a conical taper, a roughened surface and longitudinal ribs.

12 Claims, 2 Drawing Sheets

WRIST PROSTHESIS

BACKGROUND OF THE INVENTION

The invention relates to a wrist prosthesis with a radial part having a shaft that can be received in the distal region of the radial medullary canal and fixed therein, a metacarpal part having two shafts that extend distally, one of which can be received and fixed within the proximal region of the third metacarpal bone, whereas the other can be anchored in the carpal region, and a joint connection between the radial part and the metacarpal part.

A wrist prosthesis of this kind is generally known. Of the constructions most commonly used in practice, one is described in U.S. Pat. No. 4,784,661 and others in U.S. Pat. No. 4,106,128, U.S. Pat No. 4,063,314, and U.S. Pat. No. 4,180,871. The three last publications are each concerned with wrist prostheses having a ball-joint connection between the radial and the metacarpal part. Accordingly, these wrist prostheses allow both dorsal-palmar flexion and radial-ulnar deflection plus axial rotation. The disadvantage of this joint connection is its deficient stability, denoted by the term "unconstrained" joint. The ball-joint connection in itself would be ideal, as it most closely resembles the natural wrist joint. However, if during implantation the mechanical midpoint of the ball-joint connection is not found in conjunction with the tendons present in the wrist, a one-sided load is imposed on the joint connection, with the consequence that it becomes incorrectly positioned and is hence subject to abrasion. This effect is particularly evident when polyethylene is used as bearing material. For this reason the useful life of such a wrist prosthesis is very limited.

The wrist prosthesis according to U.S. Pat. No. 4,784,661 has a joint connection between the radial and metacarpal parts that comprises an ellipsoidal joint element at the metacarpal part and a complementary bearing surface at the radial part. This joint prosthesis has come to be preferred over the prosthesis with ball-joint connection. However, a problematic feature of the construction according to U.S. Pat. No. 4,784,661 is that axial rotation is not ruled out, and during such rotation the ellipsoidal bearing element is lifted away from the complementary bearing surface. The same applies to angular movements outside the axes for flexion-extension and radial/ulnar deflection. The result is that the bearing surfaces wear out prematurely. The possibility of luxation is also not excluded.

SUMMARY OF THE PRESENT INVENTION

It is the object of the present invention to create a wrist prosthesis of the kind described at the outset that is characterized by a simple and abrasion-resistant joint connection between the radial and the metacarpal part, while corresponding closely to the mobility of the anatomical wrist joint.

The wrist prosthesis in accordance with the invention thus permits no axial rotation between the radial and metacarpal parts. Axial rotation instead occurs in the forearm. It has been found that the wrist itself does not need to be capable of axial rotation. On the basis of this finding, the joint connection between radial and metacarpal part can be very simply constructed, and in particular is substantially simpler than in the case of the joint according to U.S. Pat. No. 4,307,473, which likewise incorporates a ball-joint connection. Furthermore, the choice of swivel radii in accordance with the invention achieves a close approximation to the anatomical wrist. In this regard it should be kept in mind that the forces transmitted into the connective-tissue supporting apparatus per angular degree are considerably less for "dorsal/palmar" than for "radial/ulnar". Correspondingly, in the wrist prosthesis in accordance with the invention the radial/ulnar swivel radius is distinctly larger than the dorsal/palmar swivel radius. Preferably the radial/ulnar swivel radius is about 15 to 30 mm, in particular 15 to 20 mm, whereas the dorsal/palmar swivel radius is only about 2 to 5 mm, in particular 2 to 3 mm. Owing to the swivel radii chosen in accordance with the invention, the joint connection has a smaller tendency toward destabilization.

A self-centering function is achieved also provided by a rounded joint plate and a complementary bearing recess which is smaller at the edges than the central region. As the radial/ulnar angle increases, a correspondingly increasing restoring force is exerted on the joint connection. The result is the self-centering of the joint connection in the radial/ulnar plane.

An important feature of a preferred joint connection is is the swivel radius formed by a rounded joint plate disposed at the end of a metacarpal part and a complementary recess in the radial part. Accordingly, the joint connection in accordance with this feative functions without striking a stopping element during both radial/ulnar and dorsal/palmar deflection. The two angular ranges are correspondingly large.

A specific construction is also distinguished by the fact that the joint surfaces in contact with one another are always congruent in all positions relative to one another. This is not the case with the now preferentially implanted wrist prosthesis according to U.S. Pat. No. 4, 784,661, as is evident in the above comments regarding that prosthesis. That is, during axial rotation and during angular movements outside the planes for flexion-extension and radial/ulnar deflection, the ellipsoidal bearing surfaces lose contact with one another. Because the bearing or joint surfaces are no longer congruent, wear and tear is increased, in some cases to the extent of loosening the prosthesis.

In another feature of a preferred construction, a collar preferrably a set of collars of different sizes is provided, which correspond to the various joint sizes or bone dimensions.

For cement-free implantation, the wrist prosthesis is preferably made of titanium, and includes a bearing recess for the joint plate, which is shaped like a segment of a circle, is preferably part of a polyethylene, or ceramic insert. An insert made of bearing metal is also conceivable.

The rounded joint plate can also be made of ceramic or steel instead of titanium. In principle, it is also conceivable to manufacture the whole wrist prosthesis of ceramic or steel. This would have the advantage that the wrist prosthesis would be suitable for both cement-free implantation and implantation with cement.

The surface of the collar, where provided is preferably roughened. The collar can in addition be provided with longitudinal ribs on the circumference to create spongiosa spaces between the cortical substance and the collar where provided and enable the bone tissue to grow into contact with the implant surface (bony ingrowth).

An embodiment of a wrist prosthesis constructed in accordance with the invention is described with reference to the attached drawing, wherein

3

Figure 1:
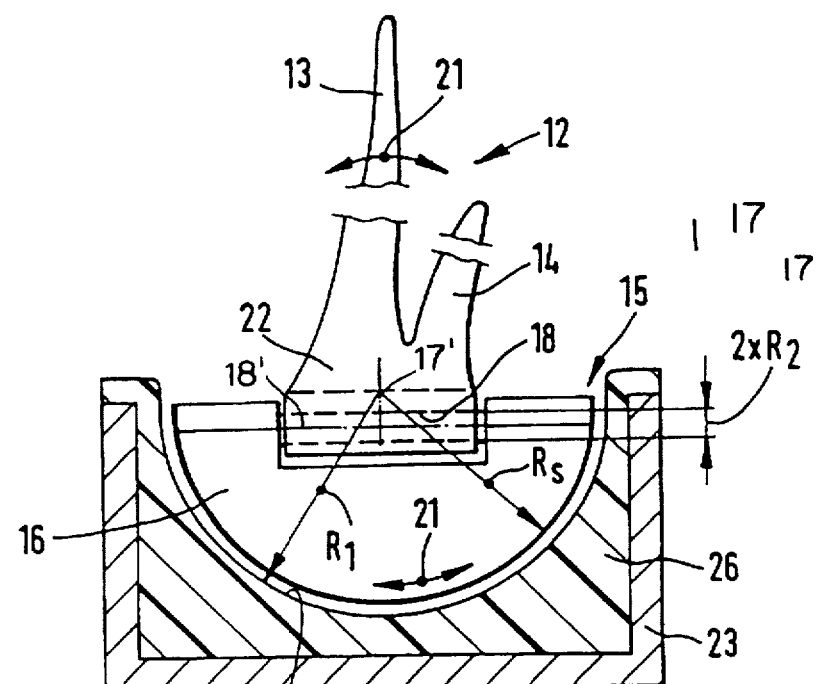
FIG. 1 is a schematic longitudinal section through a wrist prosthesis in accordance with the invention.
Figure 2:
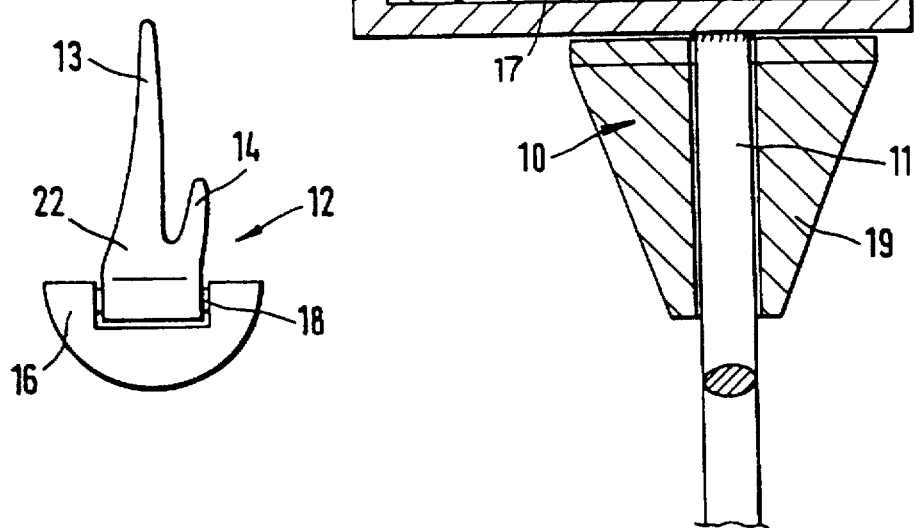
FIG. 2 is a plan view of the metacarpal part of the wrist prosthesis of FIG. 1.
Figure 3:
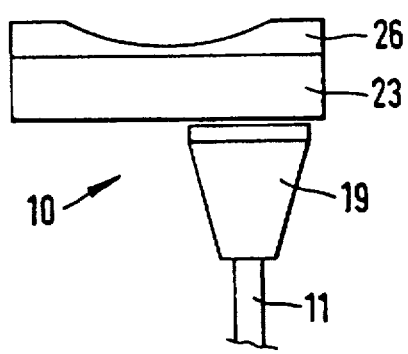
Figure 4:
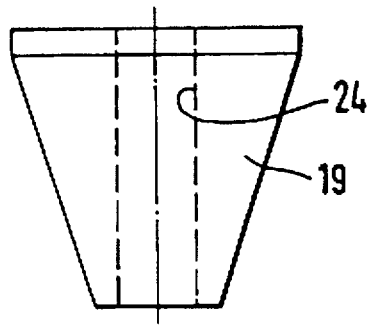
Figure 7:
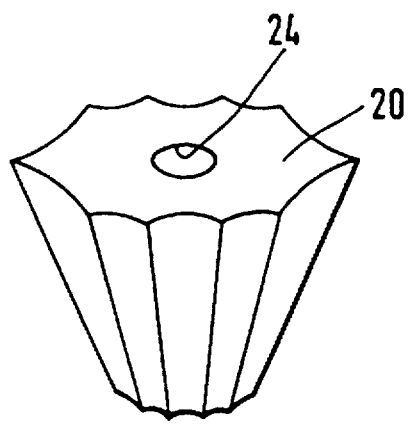
Figure 5:
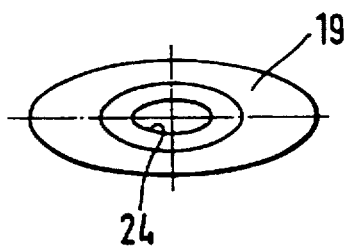
Figure 6:
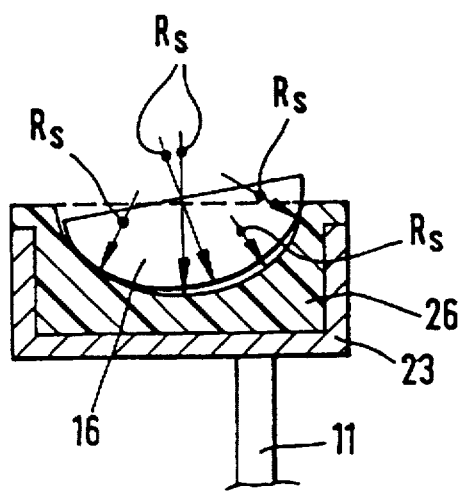

FIG. 3 is a plan view of the radial part of the wrist prosthesis of FIG. 1;

FIG. 4 is a plan view of a collar to be set into the distal region of the radial medullary canal, FIG. 5 is a bottom view of the collar of FIG. 4;

FIG. 6 is a schematic longitudinal section of the metacarpal joint part illustrates an approximately U-shaped slide-bearing surface; and FIG. 7 is a perspective plan view of an alternate embodiment of a collar.

DESCRIPTION OF THE ILLUSTRATED EMBODIMENT

In FIG. 1, a preferred embodiment of a wrist prosthesis is shown in schematic longitudinal section, with a radial part having a shaft 11 that can be received by and fixed within the distal region of the radial medullary c anal (not shown here). This shaft 11 is rod-like in shape, with an elongated oval cross section. This cross section corresponds to a similarly shaped axial bore through a collar like that shown in FIGS. 4, 5 or 7, which can be slid over the shaft 11 and placed in the distal region of the radial medullary canal. Said collar is identified by the reference numeral 19 in FIGS. 4, 5 by 20 in FIG. 7.

The wrist prosthesis includes a metacarpal part 12 with two distally extending shafts 13 and 14 of different lengths, the longer of which is to be received by and fixed within the proximal region of the third metacarpal bone. The shorter shaft is anchored in the carpal region, (preferably in the scaphoid bone). In this regard the design is known per se. Between the metacarpal part 12 and the radial part 10 is disposed a joint connection 15. This is biaxial in such a way as to permit, firstly, dorsal/palmar flexion and, secondly, radial/ulnar deflection corresponding to the double-headed arrow 21. The construction is designed such that the radial/ ulnar swivel radius $R_1$ is larger than the dorsal/palmar swivel radius $R_2$. Preferably, the radial/ulnar swivel radius $R_1$ is greater than the dorsal/palmar swivel radius $R_2$ by a factor of about 5 to 15, in particular about 10. The radial/ulnar swivel radius $R_1$ is defined by the interplay between a rounded joint plate 16, shaped like a segment of a circle, at the proximal end of the metacarpal part 12 and a complementary bearing recess 17 at the distal end of the radial part 10. In correspondence with the shape of the joint plate 16, the complementary bearing recess 17 is a groove with approximately circular floor with a common axis 17.

The two metacarpal shafts 13 and 14 are coupled to the rounded joint plate 16 by way of a flat connection element 22, mounted on a joint axle 18 extending from "radial" to "ulnar" which defines the dorsal/palmar swivel radius $R_2$. That is, the dorsal/palmar swivel radius $R_2$ equals half the diameter of the joint axle 18 as shown by axis 18.

The said bearing recess 17 to receive the rounded joint plate 16 in the embodiment shown here is part of a polyethylene insert that can be fitted into a potlike receptacle made of metal, in particular titanium or titanium alloy. The above-mentioned shaft 11 is attached to the floor of the receptacle 23.

As shown in FIG. 6, the radius $R_S$ of the rounded joint plate 16 and the corresponding radius of the complementary bearing recess 17 can be smaller at the edges than in the central region, in particular can become continuously smaller toward the two edges, so as to form an approximately U-shaped slide-face contour of the joint plate 16 and bearing recess 17. By this means the above-mentioned

4 self-centering of the joint connection in the radial/ulnar plane is achieved.

In addition, both FIG. 1 and FIG. 6 make clear that the joint connection 15 is offset in the ulnar direction from the axis of the radial shaft 11.

Onto the shaft 11 disposed on the radial part 10, as shown in FIG. 3, a collar 19 can be slipped so that when the radial part is in the implanted state, the collar 19 is seated in the distal region of the radial medullary canal. The collar 19 tapers conically from distal to proximal. As shown in FIG. 5, it is shaped like an elongated oval in cross section. The same applies to the axial bore 24 passing through the collar, which corresponds to the elongated oval cross section of the shaft 11. Hence the collar cannot rotate when it is in place on the shaft 11, where it makes contact with the floor of the receptacle 23.

As shown in FIG. 7, the collar 20 can be constructed with longitudinal ribs over its circumference. The longitudinal ribs are identified in FIG. 7 by the reference numeral 25. These create spongiosa spaces between cortical substance and collar 20, which ensure free passage of materials to the distal part of the bone and permit the bone tissue to grow toward and into the spaces as far as the implant surface.

The length of the longer shaft 13 on the metacarpal part 12 is about 35 to 45, in particular about 40 mm. The coupling of the shafts 13 and 14 to the joint plate 16 allows dorsal inclintion of about 7 to 10, in particular about 8°. The two shafts 13 and 14 extend approximately parallel to one another. The smaller shaft 14 has a length of about 12 to 20, in particular about 15 mm.

The length of the receptacle 23 is about 30 to 35 mm. Its width is about 12 to 20 mm, in particular about 15 to 16 mm. The cross section of the shaft 11 measures about 3×4 mm. The shaft 11 is preferably offset from the geometrical central axis not only toward the radius but also dorsally.

The cross section of the joint plate 16 and, correspondingly, of the bearing recess 17 is preferably rectangular, though the interior edges may be more or less strongly rounded.

The collar 19 or 20 extends axially for about 17 to 25 mm, in particular about 20 mm. The length of the shaft 11 is about 40 to 50, in particular about 45 mm. The height of the receptacle 23 is about 10 to 15, in particular about 12 mm.

The minimal wall thickness of the polyethylene insert or inlay within the receptacle 23 is about 2 to 5 mm.

The above dimensions are average values, from which departures may be made in individual cases. Ultimately the dimensions depend on the size of the wrist in which the prosthesis is to be implanted.

All the characteristics disclosed in the application documents are claimed as essential to the invention, to the extent that they are new to the state of the art singly or in combination.

List of reference numerals 10 radial part
11 shaft
12 metacarpal part
13 shaft
14 shaft
15 joint connection
16 joint plate shaped like a segment of a circle
17 bearing recess
18 joint axle
19 collar 20 collar
21 double-headed arrow
22 connection element
23 receptacle
24 bore
25 longitudinal rib
26 polyethylene insert

I claim:

1. A wrist prosthesis with a radial part (10) bearing a shaft (1) that is configured to be received in the distal region of the radial medullary canal fixed therein, a metacarpal part (12) including two shafts (13, 14) that extend distally, and of which a first shaft is configured to be fixed in the proximal region of the third metacarpal bone and the second shaft is configured to be anchored in the carpal region, comprising a joint connection (15) disposed between the radial part and the metacarpal part configured to produce only biaxial movement in said wrist prosthesis, said biaxial movement of said joint connection having a dorsal/palmer flexion with a swivel axis (17') and a radial/ulnar deflection with a swivel axis (18'), the radial/ulnar swivel axis having a radius ($R_1$) and said dorsal/palmer swivel axis having a radius ($R_2$) and wherein said radial/ulnar deflection includes a rounded joint plate (16) generally in the shape of a segment of a circle and disposed at the proximal end of the metacarpal part (12) and said radial part (10) having a complementary bearing recess (17) at a distal end, and said radial/ulnar swivel axis (17') is greater than said dorsal/palmer swivel radius (18').

2. The wrist prosthesis of claim 1 wherein said radial/ulnar swivel radius ($R_1$) is greater than the dorsal/palmar swivel radius ($R_2$) by a factor of 5-15.

3. The wrist prosthesis of claim 2 wherein said factor is substantially 10.

4. The wrist prosthesis of claim 1 having said rounded joint plate (16) wherein said two metacarpal shafts (13,14) are coupled to said rounded joint plate (16) with a joint axle (18) extending from said radial part to said ulnar part and forms said axis 18' and dorsal/palmar swivel radius ($R_2$).

5. The wrist prosthesis of claim 1 wherein the bearing recess (17) for the rounded joint plate (16) includes a bearing insert of a material selected from the group consisting of polyethylene, ceramic and bearing-metal.

6. The wrist prosthesis of claim 1 wherein said rounded joint plate (16) has a radius ($R_s$), and said complementary bearing recess (17) having a radius smaller than said radius ($R_s$) at the edges and extending toward a radial and ulnar edge than the central region of the recess.

7. The wrist prosthesis of claim 1 wherein said recess (17) is continuously smaller from the central region to at least one of the radial and/or ulnar edge.

8. The wrist prosthesis of claim 1 wherein said joint connection (15) is offset from the axis of said shaft (11) of said radial part in the direction of the ulnar deflection.

9. The wrist prosthesis of claim 1 includes at least one collar (19; 20) on said shaft (11) of the radial part (10).

10. The wrist prosthesis of claim 9 wherein said collar (19; 20) has a conical taper from a distal portion to a proximal portion, said collar has a circular cross-section.

11. The wrist prosthesis of claim 10 wherein said conical taper has an elongated oval cross section.

12. The wrist prosthesis of claim 10 wherein said collar (20) includes longitudinal ribs (25) over its circumference.

* * * * *